US011548841B2

United States Patent
Hima Bindu et al.

(10) Patent No.: US 11,548,841 B2
(45) Date of Patent: Jan. 10, 2023

(54) PRODUCTION OF LINEAR ALPHA OLEFINS

(71) Applicant: Indian Oil Corporation Limited, Mumbai (IN)

(72) Inventors: Vasamsetty Naga Veera Hima Bindu, Faridabad (IN); Mainak Sarkar, Faridabad (IN); Ganesh Vitthalrao Butley, Faridabad (IN); Ajay Kumar, Faridabad (IN); Sujit Mondal, Faridabad (IN); Ramesh Karumanchi, Faridabad (IN); Sarvesh Kumar, Faridabad (IN); Madhusudan Sau, Faridabad (IN); Gurpreet Singh Kapur, Faridabad (IN); Sankara Sri Venkata Ramakumar, Faridabad (IN)

(73) Assignee: INDIAN OIL CORPORATION LIMITED, Mumbai (IN)

( * ) Notice: Subject to any disclaimer, the term of this patent is extended or adjusted under 35 U.S.C. 154(b) by 0 days.

(21) Appl. No.: 17/448,965

(22) Filed: Sep. 27, 2021

(65) Prior Publication Data

US 2022/0098130 A1 Mar. 31, 2022

(30) Foreign Application Priority Data

Sep. 28, 2020 (IN) ............................. 202021042080

(51) Int. Cl.
C07C 5/52 (2006.01)
C07C 7/08 (2006.01)
C07C 7/10 (2006.01)

(52) U.S. Cl.
CPC .................. C07C 5/52 (2013.01); C07C 7/08 (2013.01); C07C 7/10 (2013.01)

(58) Field of Classification Search
CPC .... C07C 5/52; C07C 7/08; C07C 7/10; C10G 2300/1007; C10G 2400/22; C10G 3/50
See application file for complete search history.

(56) References Cited

U.S. PATENT DOCUMENTS

| 4,545,941 A | 10/1985 | Rosenburg |
| 6,727,396 B2 | 4/2004 | Gartside |
| 6,982,355 B2 | 1/2006 | Abazajian |
| 7,678,932 B2 | 3/2010 | Thurier et al. |
| 7,696,398 B2 | 4/2010 | Burdett et al. |
| 7,812,185 B2 | 10/2010 | Burdett et al. |
| 8,729,283 B2 | 5/2014 | Olson |
| 2013/0130336 A1 | 5/2013 | Olson |
| 2015/0080623 A1 | 3/2015 | Ratnasamy et al. |

FOREIGN PATENT DOCUMENTS

| EP | 2275514 A1 | 1/2011 |
| EP | 2952552 A1 | 12/2015 |
| EP | 3299440 A1 | 3/2018 |
| EP | 2609125 B1 | 12/2019 |
| WO | 2010025241 A3 | 1/2011 |

OTHER PUBLICATIONS

European Search Report for EP21198224.4 dated Feb. 9, 2022.

*Primary Examiner* — Thuan D Dang
(74) *Attorney, Agent, or Firm* — Workman Nydegger

(57) ABSTRACT

The present invention provides a novel route for synthesis and production of linear alpha olefins (LAO) and central olefins from the feedstock comprising fatty acids, triglycerides and esters of fatty acids, and mixture thereof through controlled hydrogenolysis, hydrogenation and dehydration reactions simultaneously in a hydro processing reactor containing a catalyst system having dual site—a metallic site for hydrogenation/reduction reaction under hydrogen environment, and an acidic site for conversion of alcohol to olefin via E1 or E2 reaction mechanism.

6 Claims, 3 Drawing Sheets

H₂ & catalyst

+ H₂O

HH₂ & catalyst

PRODUCTION OF LINEAR ALPHA OLEFINS

FIELD OF THE INVENTION

The present invention describes the process for production of linear alpha olefins (LAOs) and central olefins from the feedstock comprising fatty acids, triglycerides and esters of fatty acids, and mixtures thereof, through controlled hydrogenolysis, hydrogenation and dehydration reactions simultaneously over hydro-processing catalyst system.

BACKGROUND OF THE INVENTION

Linear alpha olefins and central olefins have wide applications in day-to-day life, starting from household products like detergents to lubricants in the automobile industry. They are used in the production of poly alpha olefins, synthetic lubricants, base stock for synthetic drilling fluids, alkylate aromatics, oxo alcohols, linear alkyl benzene (LABS), etc. Applications are mainly based on the carbon number, for example, low carbon number olefins have wide applications in the polymer industry, carbon number ranging from $C_{11}$ to $C_{16}$ is used for drilling fluids and LABS production, high carbon number $C_{20}$-$C_{30}$ are used in synthetic waxes.

Fatty alcohol market demand is also hand in glove with linear alpha olefins. In addition to the applications in detergents and surfactants, fatty alcohols play a vital role in cosmetic and food industry as thickeners, co-emulsifiers, etc., and also in paper sizing and industrial solvents. Biodegradability is the governing parameter for increase in demand for linear alpha olefins and central olefins. The common routes for the production of LAOs and central olefins are oligomerization, metathesis and the Fischer-Tropsch process.

Ethylene oligomerization route is the most common route for alpha olefin production, in this process ethylene molecules are oligomerized over catalyst systems such as an alkylated metal catalyst. U.S. Pat. No. 4,545,941 by Staley Continental Inc., EP2609125 by ExxonMobil Chemical Patents Inc., and US2013130336 by Energy and Environment Research Center (EERC) Foundation describe the process for production of LAOs by oligomerization route. Depending upon the catalyst systems and reactor configurations there are various technologies available for ethylene oligomerization process. However, in all the available technologies, both reactors and catalyst systems are very complex. Ethylene oligomerization produces a wide spectrum of linear alpha olefin products and therefore, extensive fractionation is required to separate the alpha olefins having different carbon numbers. Ethylene is a costly feedstock as it is primarily obtained from steam crackers units. Due to the expensive feedstock and complex process, the capital expenditure (CAPEX) and operating expenditure (OPEX) are high.

Alpha olefins are also produced through olefin-metathesis route. In olefin metathesis processes, two olefin molecules in the presence of a metathesis catalyst are converted into one or more olefins different from the reactant olefins. If the two reactant olefins are different, then the process is called "hetero-metathesis" or "cross-metathesis". If the two reactant olefins are identical, then the process is referred as "homo-metathesis" or "self-metathesis". The production of alpha olefin (hexene-1) through metathesis of butane-1 and butane-2 has been explained in U.S. Pat. No. 6,727,396B2 by ABB Lummus Global Inc. Further, production of alpha olefin (decene-1) via metathesis reaction of propylene, butane-1 and butene-2 with vegetable has been explained in U.S. Pat. No. 7,812,185B2 by Dow Global Technologies LLC and U.S. Pat. No. 7,678,932B2 by IFP Energies Nouvelles (IFPEN).

Metathesis product mixture typically comprises one or more product olefins, metal-ligand of catalyst, catalyst degradation products, reaction by-products, and unconverted reactant olefins. The metathesis product mixtures may also contain extraneous metals added as catalyst promoters or metals leached into the reaction from a catalyst support.

Homogeneous catalysts are also used for commercial metathesis process. Homogeneous catalysts are active and selective, however, there is present a problem with respect to the process economics, as the catalyst (including catalytic metal) should be recovered from the product mixture. More importantly, it has been observed that metathesis catalysts and catalyst degradation products destabilize olefin product mixtures against isomerization (double bond migration). These isomerized produces are different from the target products.

Metathesis catalysts and catalyst degradation products can destabilize olefin products against thermal and chemical decomposition during storage or at elevated temperatures. The undesirable thermal or chemical reactions that occur due to presence of metathesis catalyst or catalyst degradation products cause unrecoverable raw material losses and low product olefin yields. Such adverse effects are generally attributed to the presence of the catalytic metal(s) in the metathesis catalyst and catalyst degradation products. Accordingly, metathesis products are required to be stabilized (U.S. Pat. No. 7,696,398 by Dow Global Technologies LLC).

Similar to the olefin oligomerization process, the feedstock for metathesis process is also costly. Further, due to contamination in metathesis product as explained in previous paragraphs, elaborate purification steps are required again leading to high CAPEX and OPEX.

In the Fischer-Tropsch process, synthesis gas ($H_2$ and CO mixture) is generated from carbonaceous material viz., coal, biomass, pet coke, etc. The synthesis gas with appropriate $H_2$ to CO ratio is then subjected to Fischer-Tropsch synthesis (FTS) for generating hydrocarbon mixture. Currently, two methods are followed for FTS, the first method is high temperature process, where high fraction of olefins is generated, however, it also makes a large variety of olefin, paraffin, naphthene, aromatic, alcohol, aldehyde, carboxylic acid, and carboxylic ester isomers. The separation of all these isomers is extremely difficult and involves a number of steps, including, but not limited to, isomeric distillation, solvent extraction, and extractive distillation. The second method is low temperature synthesis where primarily normal paraffins, naphthas, and waxes are generated.

For producing alpha olefin, two-stage FTS process is deployed. In the first-stage paraffinic hydrocarbons is generated and in the second stage olefinic hydrocarbons are produced. In the 1st stage, paraffinic product is made by processing sub stoichiometric synthesis gas feed (i.e., $H_2$/CO feed ratio lower than about 2.1:1) over non-shifting catalyst. Since the $H_2$/CO usage ratio is stoichiometric, the effluent of the first stage is significantly depleted in CO. The effluent of first stage is then used to make olefinic hydrocarbons in the second stage over a shifting Fischer-Tropsch catalyst.

The iron-based shifting catalysts produce hydrocarbons from synthesis gas with high alpha olefin content even at high CO conversion levels, the undesirable water gas shift reaction associated with shifting catalysts wastes part (as much as 50%) of the CO feed by converting CO to $CO_2$.

Furthermore, in addition to high CO loss due to the water gas shift conversion of CO to $CO_2$, iron-based catalysts produce linear alpha olefins containing more than 1 and even as much as 10 wt. % oxygenates. These oxygenates are poisons to catalysts used for producing polymers and lubricants from olefins.

Further, use of non-shifting catalyst instead of shifting catalyst, also gives reasonably good conversion (up to 90% CO conversion) and yield $C_4$-$C_{20}$ alpha olefins with less than 3% oxygenates. The non-shifting catalysts refer to those catalysts which under reaction condition convert less than 5 mol % CO to $CO_2$ (U.S. Pat. No. 6,982,355 by REG Synthetic Fuels LLC).

The alpha olefin production through FTS route is significantly cost intensive since, it involves gasification process followed by two-stage FTS.

From the referred prior arts, it can be seen that attempts have been made to produce alpha olefins employing various techniques like ethylene oligomerization, olefin metathesis route and the Fischer-Tropsch process. These processes are cost intensive and increase the CAPEX and OPEX and also require further purification steps. Therefore, it is desirable to develop a novel process which addresses the above-mentioned plethora of issues.

SUMMARY OF THE INVENTION

The present invention discloses a novel route for synthesis of linear alpha olefins and central olefins from the feedstock comprising fatty acid, ester, and triglyceride of fatty acids, and/or the mixtures thereof.

TECHNICAL ADVANTAGES OF THE INVENTION

The present invention has the following advantages over the cited prior arts:
(i) Inexpensive feedstock: In the present invention the feedstock is either fatty acids or triglycerides of fatty acids or esters of fatty acids or naphthenic acid or mixtures thereof. These can be obtained either from natural sources or as byproduct of other industries. Hence, the feedstock for the present invention is much inexpensive compared to ethylene or syngas.
(ii) Simple process: The process involved in the present invention is hydrogenation followed by dehydration reaction. These two reactions occur simultaneously in the reactor system over a metal impregnated on acidic support catalyst system. So, effectively it is a single step process. Being a fixed bed reactor system, the process configuration is much simple compared to any process for alpha-olefin production known in the art. Further, it is also low-pressure process.
(iii) Targeted product: Based on the selection of feedstock targeted alpha-olefin can be produced from this process. The byproducts of this process are paraffins and internal olefins. While in other processes spectrum of linear alpha olefin products are formed and require elaborate purification steps.
(iv) Low cost: Because of inexpensive feedstock and simple process configuration, production of targeted alpha-olefins, the present process is much more cost competitive.

OBJECTIVES OF THE INVENTION

It is a primary objective of the present invention to provide a method for conversion of fatty acids, triglycerides and esters of fatty acids, naphthenic acid and or mixture thereof to linear alpha olefins and central olefins.

It is a further objective of the present invention that a single type used cooking oil (UCO) and/or blends of multiple types of UCO can be processed to obtain the feedstock for synthesis of linear alpha olefins and central olefins.

ABBREVIATIONS

Figure 1A:
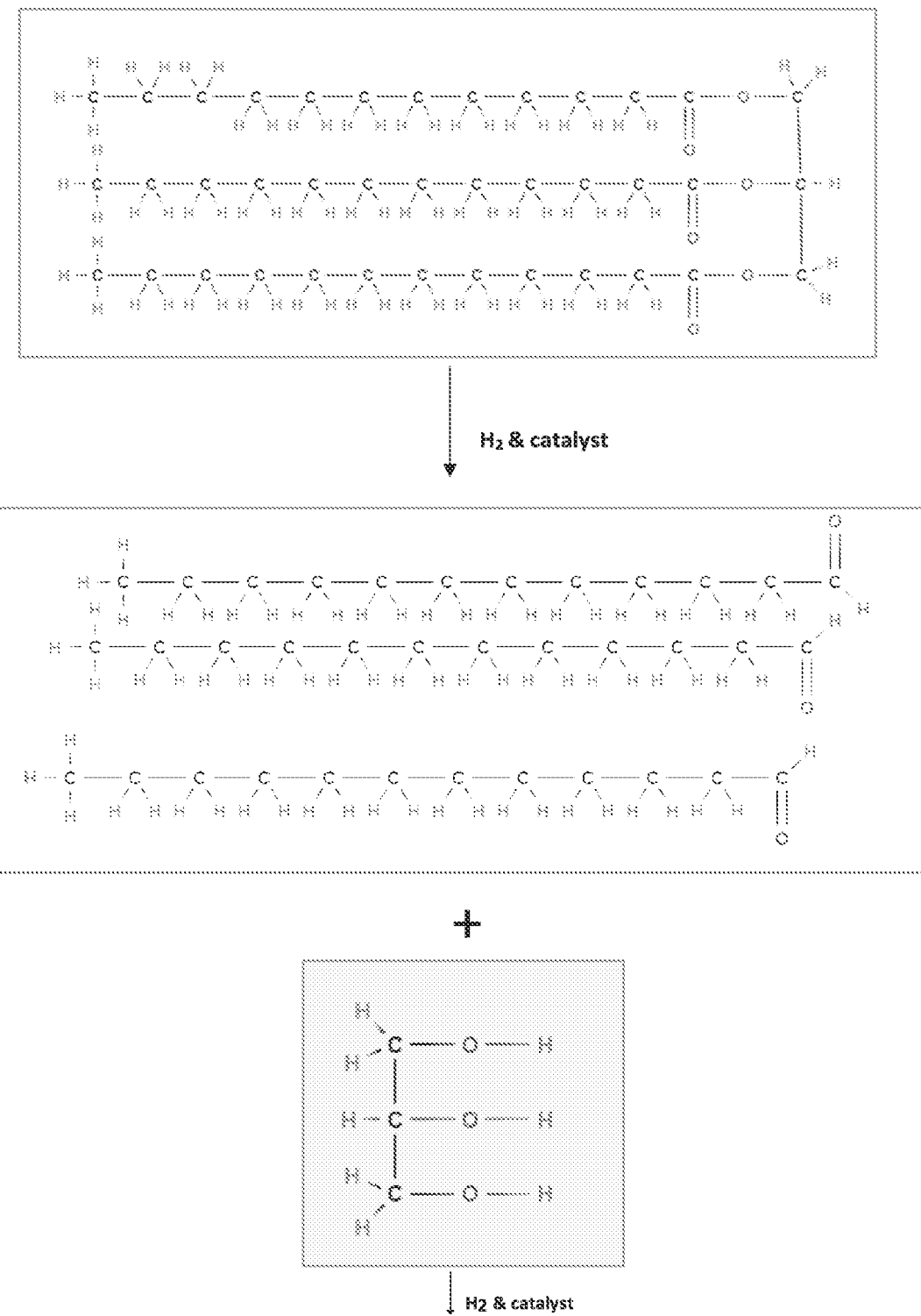
FIGS. 1A-1C illustrates the reaction scheme of the present invention.

LAO: linear alpha olefins
LABS: linear alkyl benzene
CAPEX: capital expenditure
OPEX: operating expenditure
FTS: Fischer-Tropsch synthesis
UCO: used cooking oil
MRU: micro-reactor unit
MHC: mild hydrocracking catalyst
WABT: weighted average catalyst bed temperature
LHSV: linear hourly space velocity

DETAILED DESCRIPTION OF THE INVENTION

Those skilled in the art will be aware that the present disclosure is subject to variations and modifications other than those specifically described. It is to be understood that the present disclosure includes all such variations and modifications. The disclosure also includes all such steps of the process, features of the system, referred to or indicated in this specification, individually or collectively, and any and all combinations of any or more of such steps or features.

Definitions

For convenience, before further description of the present disclosure, certain terms employed in the specification, and examples are collected here. These definitions should be read in the light of the remainder of the disclosure and understood as by a person of skill in the art. The terms used herein have their meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. It is not intended to be construed as "consists of only".

Throughout this specification, unless the context requires otherwise the word "comprise", and variations such as "comprises" and "comprising", will be understood to imply the inclusion of a stated element or step or group of element or steps but not the exclusion of any other element or step or group of element or steps.

The term "including" is used to mean "including but not limited to". "Including" and "including but not limited to" are used interchangeably.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the disclosure, the preferred methods, and materials are now described. All publications mentioned herein are incorporated herein by reference.

The present disclosure is not to be limited in scope by the specific embodiments described herein, which are intended for the purposes of exemplification only. Functionally equivalent products and methods are clearly within the scope of the disclosure, as described herein.

The process according to the present invention relates to a method for conversion of fatty acids, triglycerides and esters of fatty acids, naphthenic acid and or mixture thereof to linear alpha olefins and central olefins.

In an embodiment of the invention, the present invention provides a process for production of linear alpha olefins (LAO) and central olefins, wherein the process comprises: a) subjecting a feedstock through a hydro processing reactor containing a catalyst system having a dual site; b) performing controlled hydrogenolysis, hydrogenation and dehydration reactions simultaneously under hydrogen environment at preferred operating conditions; and c) purification and extraction of linear alpha olefins and central olefins from the product mixture along with byproducts.

The feedstock comprises fatty acids, triglycerides and esters of fatty acids, naphthenic acid and/or mixtures thereof. The feedstock can be obtained from any secondary sources consisting of fatty acids, triglycerides and esters of fatty acids, naphthenic acid and/or mixtures thereof.

In one embodiment, the present invention discloses that the feedstock for the process can be also obtained from used cooking oil (UCO) of any origin. It is further disclosed that a single type UCO and/or blends of multiple types of UCO can be used to obtain the feedstock.

The fatty acids used as feedstock can be of different types viz., aliphatic, cyclic, aromatic, branched, etc. Based on the degree of saturation, the fatty acids are classified as saturated and unsaturated. The saturated fatty acids may include, but not restricted to, lauric acid, myristic acid, palmitic acid, stearic acid, arachidic acid and lignoceric acid. The unsaturated fatty acids may include, but not restricted to, decenoic acid, undecenoic acid, dodecenoic acid, palmitoleic and oleic acid. The poly saturated fatty acids are present in the oils in addition to saturated and unsaturated fatty acids. The carbon number of the fatty acids may vary between $C_4$ and $C_{40}$.

The triglycerides of fatty acids are obtained by reaction of three molecules of fatty acids with one molecule of glycerol leaving triglyceride as main product and water as byproduct. In other words, the triglycerides are the esters of fatty acids with glycerol.

In detailed embodiment, the present invention discloses that the desired alpha olefin having particular carbon number, the feed UCO having fatty acid, ester, and triglycerides of same carbon number attached to glycerol molecule of triglycerides or same carbon number of fatty acid or ester need to be used.

In one of the embodiments, the present invention covers that that naphthenic acid derived from the mineral oil sources can be also used for synthesizing alpha olefins by this novel route, however, these alpha olefins are not LAO, we may refer to these as naphthenic alpha olefins.

In yet another embodiment, the present invention discloses that any type of triglycerides, organic acids, or the esters of organic acid derived from any sources can be used as feedstock for production of alpha or central olefin. The process comprises conversion of triglycerides and esters of fatty acid/fatty acid to LAO in presence of hydrogen over a catalyst system having dual function of metal function and acid function In the present embodiment, the present invention covers that the feedstock comprises of fatty acids, triglycerides and esters of fatty acids and mixture thereof is subjected to a catalyst system having dual site (i) metallic site for reduction reaction and (ii) acidic site for hydrogenolysis reaction under hydrogen environment at the preferred operating conditions gets converted to linear alpha olefins and central olefins along with byproducts. The reactor outlet can be further subjected to purification and alpha olefins/central olefins can be recovered from the product mixture. The product thus obtained may contain mixtures of alpha and central olefins having different carbon numbers can be separated by methods known in the art. One of these methods can be freezing the mixture, since the alpha olefins and central olefins of different carbon numbers have different freezing points. The byproducts comprise saturates, aromatics and glycerol.

In one embodiment the present invention discloses, that instead of dual functionality, two catalysts systems having separate functionality can be stacked in a single reactor or in two different reactors. In any case the catalyst with metal site should be prior to the catalyst having acidic site.

In yet another embodiment, the present invention discloses that the metal site for hydrogenation/reduction reaction of triglycerides and esters of fatty acids/fatty acids to LAO comprises transition metals from either Group VI or Group VIII or from both Group VI and VIII and dehydrogenolysis in the presence of acidic sites. Acidic sites can be provided by solid acids like zeolite, amorphous silica-alumina, ion-exchange resins, super acids, etc. It is further disclosed that the metallic site and the acidic site can be combined in a single catalyst called dual site catalyst. In the same embodiment it is also disclosed that any commercial hydrocracking catalyst can be used for this purpose. For further clarity it is also claimed that separate hydro processing catalyst (having metal site only) and zeolite base catalyst (having acidic site only) loaded in stack mode or in two separate reactors can be also used for this process.

Figure 1B:
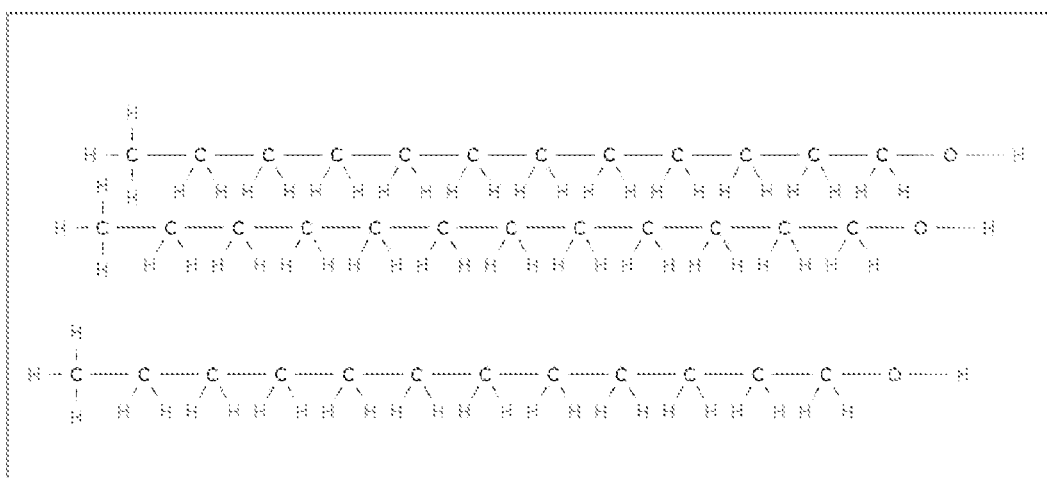
Figure 1B:
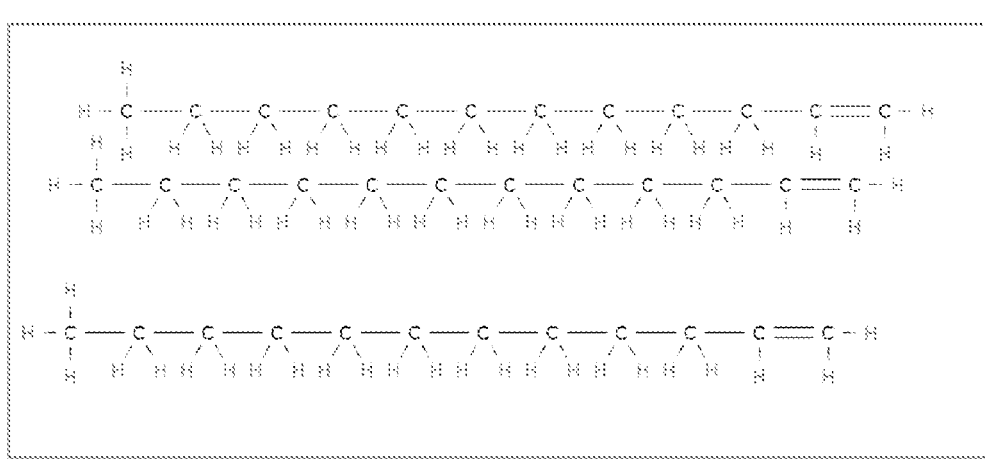
Figure 1B:
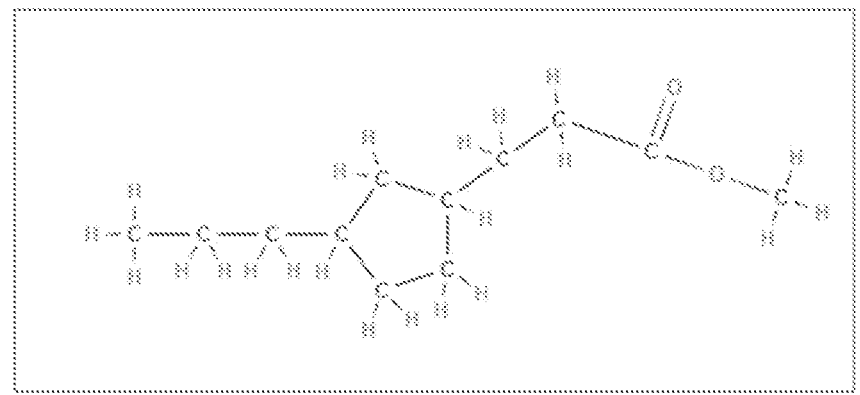
Figure 1C:
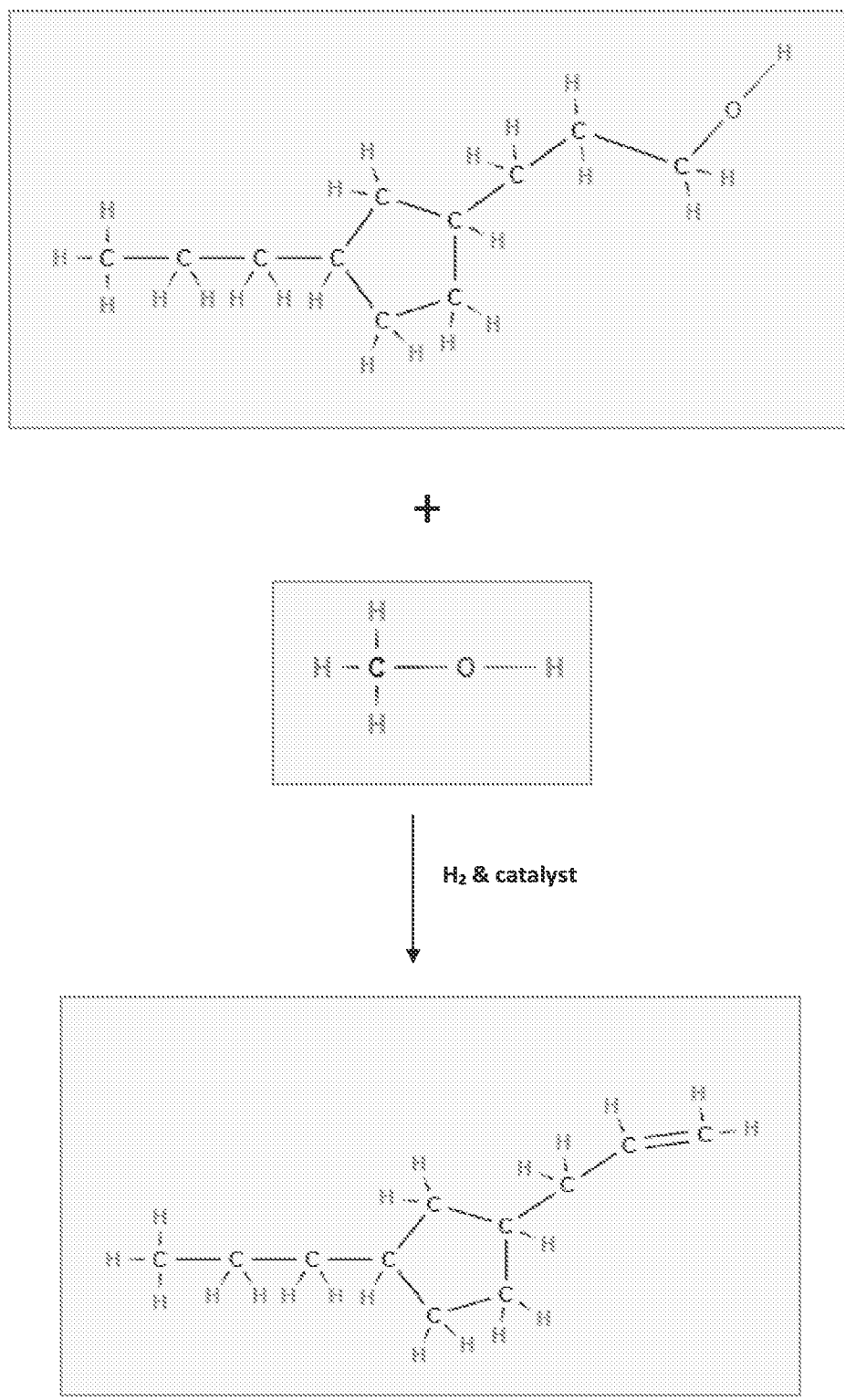

In one embodiment it is claimed that the valence state of metal in the catalyst system can be in zero state or in +2/+3 state. If the metal in the catalyst is active in zero state, then the catalyst needs to be reduced for activation purpose, however, if the metal of the catalyst system is active in +2/+3 state then the catalyst needs to be pre-sulfided for activation purpose. The reaction scheme followed in the present invention is illustrated in FIGS. 1A-1C.

In one embodiment, the present invention discloses that the reduction reaction over catalyst in hydrogen environment is very fast and therefore without proper operating condition the olefins generated in the reactor may get further reduced to alkanes.

In another embodiment, the present invention discloses that the operating pressure is preferably between 1 and 100 bars, more preferably between 1 and 50 bars and most preferably between 2 and 30 bars. The contact time described in form of liquid hourly space velocity (LHSV) is preferably between 0.1 and 20 $h^{-1}$, more preferably between 0.5 and 10 $h^{-1}$ and most preferably between 1 and 5 $h^{-1}$. The hydrogen to hydrocarbon ratio of the process is preferably between 5 and 500 $Nm^3/m^3$, more preferably between 5 and 100 $Nm^3/m^3$. The operating temperatures (WABT) of reactor are maintained preferably between 50 and 450° C., more preferably between 250 to 450° C. and most preferably between 300 to 425° C.

Linear alpha olefins produced by hydrogenolysis, reduction and dehydration reactions occurring simultaneously under controlled conditions to be sent for purification processes. The purification of linear alpha olefins can be done by the methods known in the art. Linear alpha olefins obtained through reaction in the present embodiment can be used as feed stock for the production of LABS, polymers, poly alpha olefins, synthetic lubricants, synthetic drilling fluids, etc.

EXAMPLES

Having described the basic aspects of the present invention, the following non-limiting examples illustrate specific embodiment thereof. Those skilled in the art will appreciate that many modifications may be made in the invention without changing the essence of the invention. Productions of linear olefins and central olefins through the reaction scheme mentioned in the present invention under controlled conditions is illustrated by the following example.

Example-1

Mixture of methyl ester of fatty-acids constituting methyl dodecanoic acid (63%), methyl myristic acid (26%), and methyl decanoic acid (11%) is processed in a fixed-bed micro-reactor unit (MRU). The MRU loaded with mild hydrocracking catalyst (MHC) is operated at following operating conditions as disclosed in Table 1.

TABLE 1

Operating Conditions for Example 1

| Sr. No. | Operating Parameters | Unit | Operating range |
|---|---|---|---|
| 1. | Weighted Average Catalyst Bed Temperature (WABT) | ° C | 350-410 |
| 2. | Hydrogen partial pressure | kg/cm² g | 10-30 |
| 3. | Linear Hourly Space Velocity (LHSV) | h$^{-1}$ | 1 |
| 4. | H$_2$ to feed ratio | Nm³/m³ | 300-1000 |

The cumulative product is collected and then analyzed. It has been observed that the conversion of fatty acid/triglycerides is ~100%. The yield (in wt. %) of different components is given below in Table 2. The carbon number of LAO, central olefin and paraffins, are in the range between $C_{10}$-$C_{16}$. The aromatics are mainly benzene derivatives.

TABLE 2

Yield in wt. % of different components

| Linear alpha olefin (wt. %) | Central Olefin (wt. %) | Paraffins (wt. %) | Aromatics (wt. %) |
|---|---|---|---|
| 2.7 | 26.6 | 59.1 | 11.6 |

Example-2

Mixture of fatty acids (i) methyl palmitic acid (40%), methyl oleic acid (45%) and methyl linoleic acid (15%) is processed in a fixed-bed micro-reactor unit (MRU). The MRU loaded with mild hydrocracking catalyst (MHC) is operated at following operating conditions as disclosed in Table 3.

TABLE 3

Operating Conditions for Example 2

| Sr. No. | Operating Parameters | Unit | Operating range |
|---|---|---|---|
| 1. | Weighted Average Catalyst Bed Temperature (WABT) | ° C | 400 |
| 2. | Hydrogen partial pressure | kg/cm² g | 15 |
| 3. | Linear Hourly Space Velocity (LHSV) | h$^{-1}$ | 1, 1.3 & 1.6 |
| 4. | H$_2$ to feed ratio | Nm³/m³ | 500-600 |

The product is collected and analyzed. It has been observed that the conversion is ~100%. The yield (in wt. %) of LAO, central olefins, and aromatics at three LHSV values is given below in Table 4. The carbon number of LAO, Central olefin & Paraffins, are in the range between $C_{16}$-$C_{18}$. The aromatics are mainly benzene derivatives.

TABLE 4

Yield in wt. % of different components

| LHSV (h$^{-1}$) | Linear alpha olefin (wt. %) | Central Olefin (wt. %) | Paraffins (wt. %) | Aromatics (wt. %) |
|---|---|---|---|---|
| 1 | 5.6 | 26.6 | 53.2 | 14.6 |
| 1.3 | 4.3 | 28.2 | 53.9 | 13.6 |
| 1.6 | 5.2 | 33.0 | 50.3 | 11.5 |

What is claimed is:

1. A process for production of linear alpha olefins (LAO) and central olefins, wherein the process comprises:
   a) sending a feedstock through a hydro processing reactor, comprising a catalyst system, wherein the catalyst system comprises a dual site catalyst, wherein the dual site catalyst comprises a metal site and an acidic site;
   b) performing controlled hydrogenolysis, hydrogenation and dehydration reactions simultaneously of the feedstock under hydrogen environment to obtain a product mixture comprising linear alpha olefins (LAO), central olefins, paraffins, and aromatics; and
   c) purifying and extracting the linear alpha olefins and the central olefins from the product mixture along with byproducts;
      wherein the feedstock is a single type used cooking oil (UCO) or blends of multiple types of UCO and the feedstock comprises fatty acids, triglycerides and esters of fatty acids, naphthenic acids, and mixtures thereof.

2. The process as claimed in claim 1, wherein the hydrogenolysis, hydrogenation, and dehydration reactions are performed at a pressure in a range of 1 to 100 bars.

3. The process as claimed in claim 1, wherein the hydrogenolysis, hydrogenation, and dehydration reactions are performed at a weighted average catalyst bed temperature (WABT) in a range of 50° C. to 450° C.

4. The process as claimed in claim 1, wherein the hydrogenolysis, hydrogenation, and dehydration reactions are performed at a hydrogen to hydrocarbon ratio in a range of 5 to 500 Nm³/m³.

5. The process as claimed in claim 1, wherein the hydrogenolysis, hydrogenation, and dehydration reactions are performed at a contact time in a liquid hourly space velocity (LHSV) in a range of 0.1 to 20 h$^{-1}$.

6. The process as claimed in claim 1, wherein the byproducts comprise saturates, aromatics and glycerol.

* * * * *